United States Patent [19]

Leon et al.

[11] 4,212,645

[45] Jul. 15, 1980

[54] HAIR DYEING COMPOSITION CONTAINING AN ARYLDIAMINE AND A SUBSTITUTED CATECHOL

[75] Inventors: Nicholas H. Leon, Isleworth, England; Guy A. G. Ricketts, Tokyo, Japan

[73] Assignee: Lever Brothers Company, New York, N.Y.

[21] Appl. No.: 885,705

[22] Filed: Mar. 13, 1978

Related U.S. Application Data

[63] Continuation-in-part of Ser. No. 870,151, Jan. 17, 1978, which is a continuation of Ser. No. 717,831, Aug. 25, 1976, abandoned, which is a continuation-in-part of Ser. No. 539,760, Jan. 9, 1975, abandoned.

[30] Foreign Application Priority Data

Jan. 18, 1974 [GB] United Kingdom ............... 2507/74

[51] Int. Cl.$^2$ ............................................. A61K 7/13
[52] U.S. Cl. .................................................. 8/406
[58] Field of Search ........................... 8/10.2, 11, 32

[56] References Cited

U.S. PATENT DOCUMENTS

| 2,162,458 | 6/1939 | Lehmann | 8/10.2 |
|---|---|---|---|
| 3,251,742 | 5/1966 | Soloway | 8/10.2 |
| 3,331,781 | 7/1967 | Kalopissis et al. | 8/10.2 X |
| 3,415,608 | 12/1968 | Tucker | 8/10.2 |
| 3,485,568 | 12/1969 | Kalopissis | 8/10.2 |
| 3,488,138 | 1/1970 | Iscowitz | 8/10.1 |
| 3,558,259 | 1/1971 | Kalopissis et al. | 8/10.2 |

FOREIGN PATENT DOCUMENTS

| 1206679 | 8/1959 | France | 8/10.2 |
|---|---|---|---|
| 710134 | 6/1954 | United Kingdom | 8/10.2 |
| 754949 | 8/1956 | United Kingdom | 8/10.2 |
| 827439 | 2/1960 | United Kingdom | 8/10.2 |

OTHER PUBLICATIONS

Burton, J. Soc. Cos. Chem., 2, (1951), pp. 240–244.
Burton et al., J.S.D.C., (1950), 66:474–478.
Balsam et al., Cosmetics, Science and Technology, vol. 2, Wiley Interscience, New York, (1972), pp. 306–311.

*Primary Examiner*—Norman Morgenstern
*Assistant Examiner*—Vera C. Clarke
*Attorney, Agent, or Firm*—James J. Farrell; Melvin H. Kurtz; Michael J. Kelly

[57] ABSTRACT

A composition for use in the dyeing of keratinous fibre such as hair includes an aqueous anaerobic solution of an aryldiamine and a substituted catechol. Optionally, an aromatic coupling agent can also be incorporated in the composition to modify the shade of color produced. Anaerobic storage conditions can, for example, be maintained by packing the composition in an aerosol container with a halocarbon propellant.

5 Claims, No Drawings

HAIR DYEING COMPOSITION CONTAINING AN ARYLDIAMINE AND A SUBSTITUTED CATECHOL

This application is a continuation-in-part of applicants' copending application Ser. No. 870,151, filed Jan. 17, 1978 which is a continuation of Ser. No. 717,831, filed Aug. 25, 1976 (now abandoned) which is a continuation-in-part of Ser. No. 539,760, filed Jan. 9, 1975 (now abandoned).

The invention relates to compositions for dyeing keratinous fibres, and more particularly to hair colourants.

For almost a century, p-phenylenediamine and p-toluylenediamine have both been recognised as primary intermediates in the dyeing of the hair. When mixed with hydrogen peroxide and applied to the hair, a proportion of the mixture migrates into the hair shaft and there reacts to form a permanent brown colour. However, this procedure suffers from three disadvantages: firstly, the need to keep the intermediate and oxidising agent separate until immediately prior to use, secondly, the possible damage to the hair that might be caused by excess peroxide in, for example, and improperly mixed product, and thirdly, the undesirably long time required for the dyeing process to be completed.

Certain other substituted benzene compounds such as 2, 4-diaminophenol have also been known for many years as useful in the dyeing of hair by the formation of a permanent colour within the hair shaft after reaction with atmospheric oxygen. This principle is well established and is discussed, for example in Venkataraman K, (1971), "The Chemistry of Synthetic Dyes," Volume 5 at page 475 et seq.

In spite of the considerable amount of research which has been conducted in this field it has hitherto not been possible to provide a system based on an autoxidation reaction which will impart to the hair an intense brown or nearly black colour.

We have now discovered that certain substituted dihydroxy benzene compounds together with certain oxidation dye bases can successfully be employed to impart permanent dark or intense colours to the hair especially in the absence of a peroxide or metal peroxides commonly used in the bleaching and dyeing of hair.

By "permanent" we mean that the colour of the hair remains intense after at least eight washes, but with further washing, the intensity of colour may diminish as is usual when "permanent" dye systems are employed to colour the hair.

Accordingly, the invention provides a composition for use in the dyeing of keratinous fibres comprising an anaerobic mixture of an aryldiamine

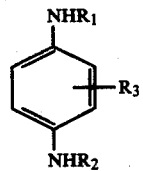

where R$_1$ and R$_2$ are hydrogen, C$_1$ to C$_4$ alkyl or C$_1$ to C$_4$ alkoxy and where R$_3$ is C$_1$ to C$_4$ alkyl or C$_1$ to C$_4$ alkoxy; and a substituted catechol having the structure:

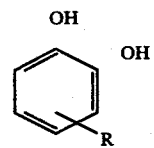

where R is amino, C$_1$ to C$_4$ alkylamino, C$_1$ to C$_4$ alkyl, C$_1$ to C$_4$ alkoxy, C$_1$ to C$_4$ hydroxyalkyl, C$_1$ to C$_4$ aminoalkyl or C$_1$ to C$_4$ alkoxy alkyl.

The invention also provides a method for dyeing hair which comprises applying to the hair a composition comprising a mixture of an aryldiamine and a substituted catechol as herein defined and allowing these ingredients to react in the presence of atmospheric oxygen.

The diamine or the salt thereof which forms part of the anaerobic mixture according to the invention has the structure:

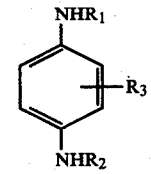

where R$_1$ and R$_2$ are hydrogen, C$_1$ to C$_4$ alkyl or C$_1$ to C$_4$ alkoxy and where R$_3$ is C$_1$ to C$_4$ alkyl or C$_1$ to C$_4$ alkoxy; if desired two or more of these aryldiamines can be present in the composition according to the invention.

The preferred aryldiamine is 2-methyl-1,4-diaminobenzene (also known as p-toluylenediamine) including its salts such as the sulphate or the hydrochloride.

Further Examples of aryldiamines are:
2-ethyl-1,4-diaminobenzene
2-n-propyl-1,4-diaminobenzene
2-isopropyl-1,4-diaminobenzene
2-n-butyl-1,4-diaminobenzene
4-amino-1-(N-ethylamino)benzene
1,4di-(N-ethylamino)benzene
4-(N-propylamino)-1-(N-ethylamino)benzene
2-ethyl-1,4-diaminobenzene
2-n-propyl-1,4-diaminobenzene
2-amino-5-(N-methylamino)toluene
5-amino-2-(N-methylamino)toluene
2-ethyl-1,4-di(N-ethylamino)benzene
4-(N-hydroxyethylamino)aniline
2-methyl-4-(N-hydroxyethylamino)aniline
3-methyl-4-(N-hydroxyethylamino)aniline
1,4-diaminobenzene(N-hydroxymethyl-N$^1$-hydroxyethyl)
2-methyl-1,4-(N-hydroxymethyl-N$^1$-hydroxyethyl)-diaminobenzene
3-methyl-1,4-(N-hydroxymethyl-N-$^1$-hydroxyethyl)-diaminobenzene
3-hydroxypyropyl-1,4(N-hydroxymethyl-N$^1$-hydroxypropyl)diaminobenzene
2hydroxymethyl-1,4-di-(N-methylamino) benzene The substituted catechol which also forms part of the anaerobic mixture according to the invention has the structure:

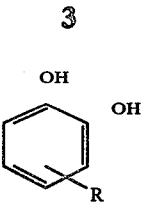

where R is amino, $C_1$ to $C_4$ alkylamino, $C_1$ to $C_4$ alkyl, $C_1$ to $C_4$ alkoxy, $C_1$ to $C_4$ hydroxyalkyl, $C_1$ to $C_4$ aminoalkyl or $C_1$ to $C_4$ alkoxyalkyl; if desired, two or more of these substituted catechols can be present in the composition according to the invention.

The preferred substituted catechols according to the invention are substituted at the 3 or the 4 position and examples of these are:
3-methylcatechol
4-methylcatechol
4-n-propylcatechol
3-isopropylcatechol
4-isopropylcatechol
3-methoxycatechol
4-t-butylcatechol
4-aminocatechol
4(N-methyl)aminocatechol Further examples of substituted catechols are:
1,2-dihydroxy-4methoxybenzene
1,2-dihydroxy-4-ethoxybenzene
1,2dihydroxy-4-propoxybenzene
1,2-dihydroxy-4-isopropoxybenzene
1,2-dihydroxy-4-butoxybenzene
1,2-dihydroxy-4-isobutoxybenzene
1,2-dihydroxy-4-sec.butoxybenzene
1,2-dihydroxy-4-tert.butoxybenzene
1,2-dihydroxy-4-methylbenzene
1,2-dihydroxy-4-ethylbenzene
1,2-dihydroxy-4-propylbenzene
1,2-dihydroxy-4-isopropylbenzene
1,2-dihydroxy-4-butylbenzene
1,2-dihydroxy-4-isobutylbenzene
1,2-dihydroxy-4-sec.butylbenzene
1,2-dihydroxy-4-tert.butylbenzene
α-amino-1,2-dihydroxy-4-methylbenzene
α-amino-1,2-dihydroxy-4-ethylbenzene
β-amino-1,2-dihydroxy-4-ethylbenzene
α-amino-1,2-dihydroxy-4-propylbenzene
β-amino-1,2-dihydroxy-4-propylbenzene
γ-amino-1,2-dihydroxy-4-propylbenzene
α-hydroxy-1,2-dihydroxy-4-methylbenzene
α-hydroxy-1,2-dihydroxy-4-ethylbenzene
β-hydroxy-1,2-dihydroxy-4-ethylbenzene
α-hydroxy-1,2-dihydroxy-4-propylbenzene
β-hydroxy-1,2-dihydroxy-4-propylbenzene
γ-hydroxy-1,2-dihydroxy-4-propylbenzene
α-hydroxy-1,2-dihydroxy-4-butylbenzene
β-hydroxy-1,2-dihydroxy-4-butylbenzene
γ-hydroxy-1,2-dihydroxy-4-butylbenzene
δ-hydroxy-1,2-dihydroxy-4-butylbenzene
α-amino-1,2-dihydroxy-4-butylbenzene
β-amino-1,2-dihydroxy-4-butylbenzene
γ-amino-1,2-dihydroxy-4-butylbenzene
δ-amino-1,2-dihydroxy-4-butylbenzene
1,2-dihydroxy-4-(NN-dimethylamino)-benzene
1,2-dihydroxy-4-(NN-diethylamino)-benzene
1,2-dihydroxy-4-(NN-dipropylamino)-benzene
1,2-dihydroxy-4-(NN-dibutylamino)-benzene
1,2-dihydroxy-4-(N-methyl-N-ethylamino)-benzene
1,2-dihydroxy-4-(N-methyl-N-butylamino)-benzene
1,2-dihydroxy-4-(N-methyl-N-propylamino)-benzene
1,2-dihydroxy-4-(N-methyl-N-hydroxymethylamino)-benzene
1,2-dihydroxy-4-(N-ethyl-N-hydroxyethylamino)-benzene
1,2-dihydroxy-4-(N-propyl-N-hydroxypropylamino)-benzene
1,2-dihydroxy-4-(N-butyl-N-hydroxybutylamino)-benzene
1,2-dihydroxy-4-(N-methyl-N-hydroxyethylamino)-benzene
1,2-dihydroxy-4-(N-methyl-N-hydroxypropylamino)-benzene
1,2-dihydroxy-4-(N-methyl-N-hydroxybutylamino)-benzene In contrast to substituted catechols such as the foregoing, we have found that unsubstituted catechols, i.e. 1,2-dihydroxybenzene, when employed with an aryldiamine as herein defined will not impart to the hair the desired intense brown or nearly black colour. Accordingly, unsubstituted catechol is excluded from the invention as herein defined.

In order to facilitate preparation of the mixture of the aryldiamine and the substituted catechol and also to ensure uniform dyeing when these ingredients are applied to the hair, it is convenient to prepare aqueous solutions of each ingredient together with sufficient of a buffer to provide an anaerobic aqueous mixed solution having a pH of from 6 to 10, preferably 7 to 9. A suitable buffer for this purpose is a phosphate buffer, but it is to be understood that the use of other buffers for adjustment of pH are not excluded. Optionally, polar organic solvents, such as isopropyl alcohol, may be added to aid solution of the aryldiamine and the substituted catechol.

The proportions of both the aryldiamine and the substituted catechol in solution usually forms from 0.1 to 6%, preferably 0.5 to 3% by weight of the composition.

The molar ratios of aryldiamine to substituted catechol can be from 1:8 to 4:4, the preferred molar ratio being 1:2 to 1:4.

Our experiments have shown that some of the substituted catechols are capable of dyeing hair in the absence of an aryldiamine, but our measurements have confirmed that the colours produced are too pale to be considered as useful in producing a dark colour, especially grey, brown, blue or black.

In general, it can be said that those compositions which dye blond Italian "Blue String" Virgin hair at a liquor ratio of 2:1 (dye solution to hair w/w) for up to 20 minutes to give an L value of about 55 or lower are preferred compositions according to the invention.

It should be explained that the intensity of the colouration produced by a dyestuff is measured in terms of L co-ordinate value (reflectance) of the Adams Chromatic Value System as adapted by R. S. Hunter. L, a reflectance parameter, is related to Y, the well known chromaticity co-ordinate, by the expression: $L = 100\sqrt{Y}$. Y is defined in "Colour in Business Science and Industry" by Judd and Wyszecki published by J. Wiley & Sons (1963). Spectral reflectance curves are measured on a Bausch and Lomb Spectronic 505 Ultraviolet spectrometer on chopped hair (in order to eliminate the specular components). The white reflectance substandard used is a clean titanium dioxide surface. Hunterlab valves are calculated using the CIE 10° observer and CIE Standard Illuminant C. The derivation of the "Hunterlab" notation is fully described in ASTM Standards Part 21

(1965) published by the American Society for Testing and Materials at page 270-273.

By way of example, we list below some of the L values obtained using certain combinations of an aryldiamine and a substituted catechol according to the invention as compared with use of substituted catechol alone.

| Substituted catechol | L Values | |
|---|---|---|
| | Substituted catechol alone (0.1M) | Substituted catechol (0.1M) + p-toluylene diamine (0.2M) |
| 3-methylcatechol | > 85 | 28.5 |
| 4-methylcatechol | 71.3 | 19.2 |
| 4-n-propylcatechol | > 85 | 29.1 |
| 3-isopropylcatechol | 63.4 | 29.1 |
| 4-isopropylcatechol | 69.6 | 24.3 |
| 3-methoxycatechol | 57.9 | 35.5 |
| 4-t-butylcatechol | 65.5 | 34.9 |

(The L valve using p-toluylene diamine alone is > 85)

It will be noted that where an L value of 55 or more was recorded, the dye was unsatisfactory. The lower the L value, the more intense is the colour produced.

The corresponding hair colours obtain after application to the hair of a substituted catechol (0.1 M) and p-toluylene diamine (0.2 M) mixture were as follows:

| Substituted catechol | Colour on hair |
|---|---|
| 3-methylcatechol | reddish brown |
| 4-methylcatechol | greyish brown |
| 4-n-propylcatechol | dark greenish brown |
| 3-isopropylcatechol | brown |
| 4-isopropylcatechol | dark blue |
| 3-methoxycatechol | medium brown |
| 4-t-butylcatechol | greenish brown |

The composition according to the invention can also contain other aromatic compounds (known as 'couplers') whose presence can vary the final colour or shade of the hair or other keratinous fibres. Examples of 'couplers' are:
2,4-diaminophenol
2,4-diaminotoluene
resorcinol
m-phenylenediamine
2,4-diaminoanisole
m-aminophenol
4methyl-3-aminophenol
α-naphthol
m-methoxyphenol
6-methyl-3-aminophenol
2,5-xylenol
2,6-xylenol
1-phenyl-3-methylpyrazolone
catechol The proportion of the coupler, when present, in the solution containing the arylamine and the substituted catechol usually does not exceed 6% and can be considered of value when present within the range 0.1 to 6%.

The molar ratios of the aryl diamine to the coupler can be from 0 to 1:2.

In order to illustrate the variety of shades that can be obtained by a specified aryldiamine, and specified substituted catechol with a variety of couplers, we list below, by way of example, some of the colours produced when applied to blond hair.

| 4-isopropyl catechol (0.1M) + p-toluylenediamine (0.2M) + 'COUPLER' (0.1M) | Colour on hair |
|---|---|
| 2,4-diaminophenol | medium brown |
| 2,6-diaminotoluene | bluish grey |
| 2,4-diaminotoluene | greenish grey |
| resorcinol | bluish grey |
| NO 'COUPLER' (Control) | dark blue |

It will be appreciated that development of colour in the hair is dependant on the interaction of the aryldiamine and substituted catechol (and 'coupler', if present) in the presence of atmospheric oxygen. Compositions according to the invention should therefore be prepared in such a manner that atmospheric oxygen is excluded until the composition is required for use in the dyeing of hair or other keratinous fibres. Antioxidants, such as sodium bisulphite and ascorbic acid, may be incorporated in compositions according to the invention in order to limit premature oxidation during storage: up to 5% by weight of these antioxidants are usually sufficient.

The means whereby anaerobic conditions are maintained can be influenced by the packaging adopted for containing and storing the composition according to the invention prior to use by the consumer. For example, when stored in a bottle or other closed container at about atmospheric pressure, the mixed solution of aryldiamine and substituted catechol, and other ingredients if present, is preferably stored under nitrogen in the presence of an antioxidant until required for use. Alternatively, when the composition is stored in a pressurised pack device such as an aerosol can, the usual halocarbon propellant mixture which enables the composition ultimately to be dispensed also serves to maintain anaerobic conditions within such a device.

It is also possible to include other ingredients in compositions according to the invention to facilitate its application to the hair or other keratinous fibre by the user. For example, thickeners such as salt or carboxymethyl cellulose may be incorporated in the mixed solution to air retention of the composition when applied, for example to the head, it being inconvenient or possibly dangerous should the dyestuff ingredients reach the face or eyes. Detergents can also be incorporated in the composition according to the invention without necessarily interfering with the dyeing process. Thus, for example, it may be convenient to include up to 20% of one or more detergent actives to assist the user in distributing the mixed solution of dyestuff ingredients throughout the hair. Foam boosters, conditioners, preservatives and perfumes can also be included in compositions according to the invention.

When hair or other keratinous fibre is to be dyed with compositions according to the invention, it is optionally first washed and then a proportion of the anaerobic mixed solution containing the aryldiamine and substituted catechol (and other ingredients as desired) applied and thoroughly rubbed in. By way of example, for a normal head of hair (about 70 g in weight) about 20 ml of an aqueous solution containing up to 0.4 M of both the aryldiamine and the substituted catechol is applied to the hair. Both the duration and temperature of application to the hair or other keratinous fibre will effect the final result obtained. In general, the longer the time and the higher the temperature of contact, the darker or more intense is the colour of the dyed hair or other fibre which finally results, but 10 to 15 minutes at room temperature is usually sufficient for the development of a desirably intense colour.

Compositions according to the invention are particularly of value in the dyeing of human hair, either attached to the head or in the form of a wig, hairpiece or switch. The compositions can however also be employed in the dyeing of other natural keratinous fibres such as wool or silk or of synthetic keratinous fibres.

The invention is illustrated by the following Examples.

EXAMPLE 1

In this example, p-toluylenediamine sulphate as the aryldiamine was mixed with 4-methylcatechol as the substituted catechol and used to dye switches of natural human hair.

Preparation of solution of dye precursors p-toluylenediamine sulphate, 22.0 g, together with 4-methylcatechol, 24.8 g, were dissolved in 1 liter of phosphate buffer to provide a concentration of 0.1 M with respect to the p-toluylenediamine and 0.2 M with respect to the 4-methylcatechol. The phosphate buffer was prepared by dissolving sodium dihydrogen orthophosphate, 13.6 g, in water, 500 ml, and isopropyl alcohol, 150 ml, was then added and the solution made up to 1 liter after adjustment of the pH with sodium hydroxide to 8.0.

The mixed solution was prepared under nitrogen and stored anaerobically until required for use.

Dyeing of Hair

A switch of Italian "Blue String" virgin blond hair (about 0.5 g) was thoroughly wetted with the anaerobic solution containing the dye precursors in a 5 cm dish open to the atmosphere. The switch was turned and agitated frequently with a glass rod during dyeing. After immersion in the dye solution for 1 hour, the hair switch was shampooed, rinsed and dried. Further switches of the same hair were dyed with p-toluylenediamine alone and with 4-methylcatechol along.

Hair treated with p-toluylenediamine alone was dyed a greyish colour while that dyed with 4-methylcatechol retained no desirable colour. When, however, the mixture of p-toluylenediamine and 4-methylcatechol was applied at room temperature for 1 hour, a very dark brown colour was produced.

EXAMPLE 2

In this Example, p-toluylenediamine sulphate as the aryldiamine was mixed with 4-methyl catechol as the substituted catechol together with a high level of detergent to form a shampoo dye product.

Preparation of Shampoo Dye

A solution of the dye precursors was prepared using pH 8.5 phosphate buffer. The solution contained by weight 0.54% p-toluylenediamine sulphate, 1.2% 4-methyl catechol and in addition 10% (active detergent basis) Empicol LE 33S.

Dyeing of Hair

Switches of Italian "Blue String" virgin blond hair were dyed according to the procedure described in Example 1. A light ash-green-brown colour resulted.

EXAMPLE 3

In this Example, p-toluylenediamine sulphate as the aryldiamine was mixed with 4-methyl catechol as the substituted catechol together with a low level of detergent and with a propellant system to give an aerosol product.

Preparation of Aerosol Hair Dye Product

A solution of the dye precursors was prepared using pH 8.5 phosphate buffer. The solution contained by weight 0.54% p-toluylene diamine sulphate, 1.2% 4-methyl catechol and in addition 1% (active detergent basis) Empicol LZV. The solution was packed with 5% Propellant 12 and 5% Propellant 114 in a pressurised pack device.

Dyeing of Hair

Switches of Italian "Blue String" virgin blond hair were dyed according to the procedure described in Example 1. A dark green colour resulted.

What is claimed is:

1. A composition for use in the dyeing of keratinous fibres which comprises an aqueous anaerobic solution of
   (i) from about 0.1 to about 6% by weight of an aryldiamine or a salt thereof having the structure

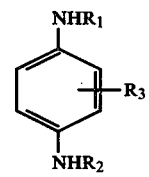

where $R_1$ and $R_2$ are selected from the group consisting of hydrogen, $C_1-C_4$ alkyl and $C_1-C_4$ alkoxy, and where $R_3$ is selected from the group consisting of $C_1-C_4$ alkyl and $C_1-C_4$ alkoxy; and
   (ii) from about 0.1 to about 6% by weight of a substituted catechol having the structure

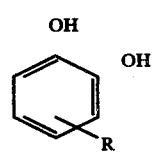

where R is selected from the group consisting of amino, $C_1-C_4$ alkylamino, $C_1-C_4$ alkyl, $C_1-C_4$ alkoxy, $C_1-C_4$ hydroxyalkyl, $C_1-C_4$ aminoalkyl and $C_1-C_4$ alkoxyalkyl, the molar ratio of aryldiamine to substituted catechol in the solution being from about 1:8 to about 4:1.

2. A composition according to claim 1, wherein the aryldiamine is selected from the group consisting of 2-methyl-1,4-diaminobenzene, its salts and mixtures thereof.

3. A composition according to claim 1, wherein the substituted catechol is selected from the group consisting of
3-methylcatechol
4-methylcatechol
4-n-propylcatechol
3-isopropylcatechol
4-isopropylcatechol
3-methoxycatechol 4-t-butylcatechol
4-aminocatechol
4(N-methyl)aminocatechol
and mixtures thereof.

4. A composition according to claim 1, wherein the solution additionally comprises from 0 to about 6% by weight of a coupler selected from the group consisting of:
2,4-diaminophenol
2,4-diaminotoluene
resorcinol
m-phenylenediamine
2,4-diamino anisole
m-aminophenol
α-naphthol
m-methoxyphenol
6-methyl-3-aminophenol
2,5-xylenol
2,6-xylenol
1phenyl-3-methylpyrazolone
catechol
and mixtures thereof; the molar ratio of aryldiamine to coupler in the solution being from 1:0 to about 1:2.

5. A method of dyeing keratinous fibres which comprises applying to the keratinous fibres an effective amount of a composition as defined in claim 1.

* * * * *